United States Patent [19]

Englaender et al.

[11] Patent Number: 4,665,218

[45] Date of Patent: May 12, 1987

[54] METHOD FOR THE PREPARATION OF ALKOXYMETHYLENE COMPOUNDS OF ACETIC ESTERS AND SUBSTITUTED ACETIC ESTERS

[75] Inventors: Fritz Englaender, Bonn; Wilhelm Vogt, Cologne, both of Fed. Rep. of Germany

[73] Assignee: Dynamit Nobel AG, Cologne, Fed. Rep. of Germany

[21] Appl. No.: 724,992

[22] Filed: Apr. 19, 1985

[30] Foreign Application Priority Data

Apr. 26, 1984 [DE] Fed. Rep. of Germany ....... 3415475

[51] Int. Cl.$^4$ .................. C07C 69/732; C07C 69/734
[52] U.S. Cl. .................................................. 560/181
[58] Field of Search ................ 560/181, 183; 556/483, 556/484; 260/453.99

[56] References Cited

U.S. PATENT DOCUMENTS

| | | | |
|---|---|---|---|
| 2,571,212 | 10/1951 | Croxall et al. | 560/181 |
| 2,722,542 | 11/1955 | Rexford | 560/183 |
| 3,515,745 | 6/1970 | Tull et al. | 560/181 |
| 3,637,812 | 1/1972 | Tull et al. | 560/181 |
| 3,639,445 | 2/1972 | Pawlowski | 560/183 |
| 3,641,057 | 2/1972 | Scharf et al. | 560/183 |
| 4,503,074 | 3/1985 | Friedman | 560/181 |

FOREIGN PATENT DOCUMENTS

| | | | |
|---|---|---|---|
| 52-68116 | 6/1977 | Japan | 560/181 |
| 620187 | 11/1980 | Switzerland . | |

OTHER PUBLICATIONS

Dominte et al., *Chemical Abstracts,* vol. 99, No. 104776t, (1983).
Fattore et al., *Chemical Abstracts,* vol. 94, No. 174325r, (1981).
Stecher et al., *The Merck Index of Chemicals and Drugs,* seventh ed., Rahway, N.J., p. 8, (1960).

*Primary Examiner*—Natalie Trousof
*Assistant Examiner*—Bruce D. Gray
*Attorney, Agent, or Firm*—Felfe & Lynch

[57] ABSTRACT

Disclosed is a method for preparation of alkoxymethylene compounds, especially methoxymethylene compounds, from substituted or unsubstituted acetic acid alkyl esters, especially methyl esters, from the corresponding hydroxymethylene compounds or their alkali salts, by reaction with excess alkanol, especially methanol, in the presence of HCl and a water-binding agent. Preferred are water-binding agents which form stable reaction products with water.

9 Claims, No Drawings

4,665,218

METHOD FOR THE PREPARATION OF ALKOXYMETHYLENE COMPOUNDS OF ACETIC ESTERS AND SUBSTITUTED ACETIC ESTERS

BACKGROUND OF THE INVENTION

The invention relates especially to an improved method for the preparation of methoxymethylene compounds of acetic acid methyl ester, which can be substituted if desired, and of ethoxymethylene compounds from unsubstituted and substituted acetic acid ethyl esters. In particular, methoxymethylene compounds of malonic acid dimethyl ester, and also of cyanoacetic acid methyl ester, methoxyacetic acid methyl ester and acetic acid methyl ester, are prepared by this method.

Accordingly, ethoxymethylene compounds especially of malonic acid diethyl ester, and also of cyanoacetic, methoxyacetic, ethoxyacetic and acetic acid ethyl esters can be prepared. If needed, alkoxymethylene compounds of the above-named esters can also be prepared, which have saturated aliphatic alkoxy groups of 1 to 6 carbon atoms, and which very preferentially have in the ester groups the same saturated or unsaturated alkyl moieties of 1 to 6 carbon atoms as in the alkoxymethylene group.

A special advantage of the process is that enol ethers can be prepared with hydroxymethylene compounds which are stable only as sodium salts, such as the sodium salts of hydroxymethylene acetic acid methyl ester and hydroxymethylene methoxyacetic acid methyl ester.

It is known to react the methoxymethylene compound of malonic acid dimethyl ester with trimethylorthoformate in the presence of acetic anhydride and zinc chloride (Claisen, A. 297 1 (1897), German Fed. publication AS No. 24 26 964). A disadvantage of the process is, however, that it requires long reaction times and a great amount of distillation if good yields are to be achieved.

In accordance with German Fed. publication OS No. 18 00 352, malonic acid dimethyl ester is reacted with carbon monoxide in the presence of sodium methylate and methanol to the sodium salt of hydroxymethylene malonic acid dimethyl ester, and this is transformed in an inert solvent, such as toluene, by reaction with dimethylsulfate to methoxymethylene malonic acid dimethyl ester. In addition to the high toxicity of the dimethylsulfate, the reaction has the disadvantage that only one methyl group of the dimethylsulfate is utilized. Alcohols instead of dialkylsulfat do not form alkoxymethylene compounds.

The problem therefore existed of preparing alkoxymethylene compounds, especially methoxymethylene compounds, from acetic acid esters and substituted acetic acid esters having 1 to 6 carbon atoms in the alkyl moiety of the ester group, especially from methyl esters, in a simple manner with a high yield.

THE INVENTION

It has been found that alkoxymethylene compounds, especially methoxymethylene compounds, of acetic acid esters and substituted acetic acid esters can be prepared in a simple manner with a high yield by reacting excess alkanol in the presence of HCl and a water-binding agent with the particular hydroxymethylene acetic acid alkyl ester, especially hydroxymethylene acetic acid methyl ester and/or its alkali salts.

The subject matter of the invention is therefore a method for the preparation of alkoxymethylene compounds of substituted or unsubstituted acetic acid alkyl esters, especially acetic acid methyl esters, which is characterized by reacting excess alkanol, especially methanol, in the presence of HCl and a water-binding agent, with the corresponding hydroxymethylene compound of the substituted or unsubstituted acetic acid alkyl ester or its alkali.

As substituted acetic acid alkyl esters especially are cyanoacetic acid esters, alkoxyacetic acid esters, wherein alkoxy group and alkyl group of the esters are straight or branched chains of 1 to 6 carbon atoms, further phenyl- or naphthylacetic acid esters or acetic acid alkyl esters substituted by the group —COOR, which are malonic acid esters.

The method is especially valuable for the preparation of methoxymethylene malonic acid dimethyl ester. In addition, the method can be employed for the technical production of ethoxymethylene malonic acid diethyl ester as well as of methoxymethylene compounds of cyanoacetic acid methyl ester, methoxyacetic acid methyl ester, and acetic acid methyl ester, and lastly for the preparation of any desired alkoxymethylene compounds.

The method is practiced with excess alkanol. Preferably, the alkanol is used as a solvent or suspending agent. The preferred alkanol is methanol for the preparation of alkalisalts of methoxymethylene compounds. At least 1.1 moles of alkanol is preferably present per mole of reactant. For the preparation of ethoxymethylene compounds, ethanol is to be chosen, and, for the preparation of additional alkoxymethylene compounds, the particular corresponding alkanol. Preferably, the alkyl group of the alkoxymethylene group and the alkyl group in the ester moiety are to be the same.

Preferred as starting substances are the alkali salts of the particular alkoxymethylene compounds, especially the sodium salts. Very preferably, the method is performed directly after the preparation of the alkali-alkoxymethylene compounds by formylating the ester with carbon monoxide or alkylformate in alkanol in the presence of alkali alcoholate. The particular alkanol serves in that case, too, as the solvent. This is especially true of the reaction solution of sodium hydroxymethylene malonic acid dimethyl ester in methanol.

In the process, HCl is to be present in excess. The HCl must therefore be put in in gas form, unless it is formed by the reaction of the water-binding agent. During the reaction, the concentration of the free HCl in the reaction mixture is to amount to from 0.5 to 10%, preferably 3.0 to 6.0%, by weight, referred to the amount of the reactant in the reaction mixture.

Suitable water-binding agents are those which do not release the water again during the reaction and work-up. Water-binding agents which form stable reaction products with water, which are inert in the reaction and work-up of the product, are especially suitable.

The following embodiments of the method have proven especially valuable. On the one hand, in the preparation especially of methoxymethylene compounds of substituted or unsubstituted acetic acid methyl ester, and very especially of methoxymethylene malonic acid dimethyl ester, it is possible to add methanol as well as HCl, plus an aliphatic nitrile of 2 to 6 carbon atoms, especially acetonitrile, as the water-binding agent. The acetiminomethyl ester hydrochloride forming from acetonitrile, methanol and HCl, reacts with water to form methyl acetate and ammonium chloride. In this manner the water is removed from the equilibrium and the yield of methoxymethylene malonic acid dimethyl ester is considerably improved. The nitrile is to be used in amounts of 1.02 to 2.0, preferably 1.05 to 1.25 moles, per mole of starting material.

If nitriles are used, it is desirable to use the free hydroxymethylene compounds as the starting substances.

On the other hand, tetraalkoxysilanes of 2 to 6 carbon atoms in the alkyl group, very preferably tetramethoxysilane, plus also tetraethoxysilane, can be added. If they are available, $SiCL_2(OCH_3)_2$ or $SiCL_3(OCH_3)$ can be used. In the reaction with the water, siloxanes of high molecular weight are formed, from which the enol ether can easily be destilled out. Preferably the alkoxy group of silanes corresponds to the alkoxy group of the reactants and products.

Furthermore, silicon tetrachloride reacts with alkanol to form HCl and tetralkoxysilane or condensed silanes. HCl releases the hydroxymethylene compounds from the alkali salt. Therefore, the alkali salts are preferred as starting substances, and so are the methyl esters.

Methanolic solutions are decidedly preferred, as well as tetramethoxysilane accordingly. Ethanolic solutions are preferred to produce ethoxy methylene compounds, further alkanols to form the corresponding alkoxy methylene compound. It is possible to good advantage to set out directly from the methanolic suspension of sodium hydroxymethylene malonic acid dimethyl ester or other alkali salts of hydroxymethylene acetic acid methyl ester, as obtained in the formylation of, the named unsubstituted or substituted acetic acid alkyl ester e.g., dimethylmalonate with carbon monoxide or alkyl formiate, therein alkyl means as defined before in the presence of sodium methylate. Silicon tetrachloride reacts with methanol to form HCl and tetramethoxysilane. HCl releases the hydroxymethylene compound from the sodium salt. In this manner the additional advantage is obtained that the reaction product of the formylation does not need to be isolated. The hydroxymethylene acetic acid alkyl esters reacts with alkanols, which are present in excess anyway, in the formylation stage, to form the methoxy compound in presence of said water binding agents. HCl acts as a catalyst. HCl may be formed in the reaction mixtures by reactions of silicon tetrachloride and the used alkanol. The water formed in the reaction reacts with tetraalkoxysilane to form polysiloxanes and in this manner is removed from the acetalization equilibrium.

The amount of silicon tetrachloride or tetraalkoxysilane, as the case may be, which is to be added for each mole of water that is formed, is between 0.5 and 2.0 moles. In the reaction of 0.5 mole, silicic acid theoretically forms, i.e., actually a siloxane of very high molecular weight having only a few remaining alkoxy groups; in the reaction of 2.0 moles, siloxanes form having boiling points above 200° C., predominantly $(CH_3O)_3Si\text{-}OSi(OCH_3)_3$. Polysiloxanes of very great molecular weight are undesirable, because they hold stubbornly onto reaction product in the distillation, and are hard to remove from the apparatus after distillation is completed. Polysiloxanes of very low molecular weight pass over with the reaction product when it is distilled off, and contaminate the distillate. The preferred amount of silicon tetrachloride is accordingly between 0.6 and 1.1 mole of silicon tetrachloride or tetraalkoxysilane per mole of water.

The reaction takes place generally at room temperature. However, elevated temperatures can be used, up to a maximum of 50° C. Temperatures lower than 20° C. offer no advantage. The preferred range is between 20° and 40° C.

The reaction can be performed in a closed vessel at standard pressure.

After the reaction, a neutralization is performed, the product is separated from any sodium chloride that may have formed, and is worked up, for example by distillation.

The reaction product distilled from the polysiloxanes often still contains acetals, i.e., dialkoxymethyl compounds; for example, methoxymethylenemalonic acid dimethyl ester contains amounts of dimethoxymethylmalonic acid dimethyl ester. By heating at 100° to 200° C., preferably 140° to 155° C., preferably in the presence of 0.1 to 10%, by weight, preferably 0.9 to 2.5% by weight, of an acid catalyst, such as potassium bisulfate, sulfuric acid or p-toluenesulfonic acid, methanol is split off and the enol is obtained in a nearly quantitative yield methoxy methylene malonic acid dimethylester.

The methoxymethylene compounds are valuable intermediates for the preparation of heterocyclic compounds. For example, methoxymethylenemalonic acid dimethyl ester is used for syntheses in the quinoline series (cf. Schofield, K., and J. C. E. Simpson: J. Chem. Soc. London 1946, 1033; Snyder, H. R. J.: Am. Chem. Soc. 68, 1204, 1251 (1946) and 69, 371 (1947); Duffin, G. J. and J. D. Kendall: J. Chem. Soc. London 948, 893).

EXAMPLES

EXAMPLE 1

160 g (1.0 mol) of hydroxymethylenemalonic acid dimethyl ester is dissolved in 288 g (9.0 mol) of methanol and 50 g of hydrogen chloride gas is introduced. Then 55.2 g (1.35 mol) of acetonitrile is added and the mixture is let stand for 24 hours at room temperature. Then the low-boiling substances are distilled out, dichloromethane is added to the residue, and ammonium chloride is filtered out. The filtrate is treated with 1.6 g of potassium bisulfate and heated while distilling the volatile components up to 130° C. 138 g (0.79 mol) of methoxymethylenmalonic acid dimethyl ester is obtained, corresponding to 79.3% of the theory.

EXAMPLE 2

396 g (3.0 mol) of dimethylmalonate, 170.1 g of sodium methylate and 1425 g (44.5 mol) of methanol are reacted at 60° C. and 45 bar of carbon monoxide pressure until no more carbon monoxide is absorbed. The sodium salt of the hydroxy methylene malonic acid dimethyl ester is formed. Then 382.5 g (2.25 mol) of silicon tetrachloride is added at a temperature of 25° C. To complete the reaction the mixture is let stand for another 5 hours at 25° C. By the addition of sodium methylate, the reaction mixture is adjusted to pH 2 and sodium chloride is filtered out. Methyl formate and methanol are recovered from the filtrate by distillation under standard pressure, and can be used again. By vacuum distillation a mixture of methoxymethylenemalonic acid dimethyl ester and dimethoxymethylmalonic acid dimethyl ester is obtained. The polymeric silicic acid esters remain in the residue. The distillate from the vacuum distillation is treated with 6 g of potassium bisulfate and heated at 150° C. After the removal of methanol has ended, the mixture is fractionally distilled in vacuo. 433 g of methoxymethylenemalonic acid dimethyl ester is obtained, corresponding to 82.9% of the theory with respect to the dimethylmalonate put in.

EXAMPLE 3

690 g of toluene and 90.7 g of sodium methylate are placed in an autoclave. At a temperature of 50° C. and a is slowly added. As soon as the carbon monoxide absorption has ended, a mixture of 716 g of methanol and 130 g of silicon tetrachloride is added, at a temperature of 25° C. After the reaction has ended, the acidity is brought to pH 2 with sodium methylate, and sodium chloride is removed by filtration. The low-boiling methyl formate, methanol and toluene are distilled from the filtrate at standard pressure. The reaction product has to be distilled in vacuo to free it of the polymeric silicic acid esters. 2 g of potassium bisulfate is added and the mixture is heated at 150° C. After the release of methanol has ended, a fractional distillation can be performed. 177.5 g of methoxymethylenemethoxyacetic acid methyl ester is obtained, corresponding to 76% of the theory with respect to the input methoxyacetic acid methyl ester.

EXAMPLE 4

372 g of the sodium salt of hydroxymethyleneacetic acid methyl ester is suspended in 1720 g of methanol and 305 g of silicon tetrachloride is added at 20° C. The reaction mixture is then let stand for 12 hours, and then brought to pH 2 with sodium methylate, and sodium chloride is filtered out.

After the methanol is distilled out, the residue is freed of the silicic acid esters by distillation in vacuo. 2 g of potassium bisulfate is added and the mixture is heated to 130° C. As soon as the release of the methanol has ended, a fractional distillation is performed in vacuo.

181 g of methoxymethyleneacetic acid methyl ester is obtained. Making allowance for the purity of the starting product (68%) this corresponds to a yield of 76.5% of the theory.

EXAMPLE 5

164 g of the sodium salt of hydroxymethylenecyanoacetic acid methyl ester is suspended in 320 g of methanol and 114 g of silicon tetrachloride is added at 20° C. After 13 hours, a pH of 2 is established with sodium methylate. The rest of the procedure is as described in Example 4.

The yield is 91 g of methoxymethylenecyanoacetic acid methyl ester. Making allowance for the purity of the starting product (89%), this corresponds to a yield of 65.9% of the theory.

EXAMPLE 6

160 g of diethyl malonate, 71.4 g of sodium ethylate and 322 g of ethanol are reacted with carbon monoxide at 60° C. and 45 bar. At a temperature of 85° C., 136 g of silicon tetrachloride is added to the resulting reaction mixture, which is then maintained at 25° C. for 5 hours to complete the reaction. By the addition of sodium ethylate the reaction mixture is adjusted to pH 2 and sodium chloride is filtered out. By distillation at standard pressure, ethyl formate and ethanol are recovered from the filtrate and can be reused. Vacuum distillation of the residue produces a mixture of ethoxymethylenemalonic acid diethyl ester and diethylmethylmalonic acid diethyl ester. The polymeric silicic acid esters remain in the residue as a liquid of an oily consistency at 100° C. The distillate from the vacuum distillation is treated with 1.5 g of potassium bisulfate and heated at 160° C. After all the ethanol has been released, the mixture is fractionated in vacuo.

As the first runnings some diethoxymethylmalonic acid diethyl ester is obtained, whose ethanol can be cleaved off together with the acetal of a subsequent batch.

The yield of ethoxymethylenemalonic acid diethyl ester is 144.7 g, corresponding to 67% of the theory with respect to the input diethylmalonate.

It will be understood that the specification and examples are illustrative but not limitative of the present invention and that other embodiments within the spirit and scope of the invention will suggest themselves to those skilled in the art.

We claim:

1. A method for the preparation of alkoxymethylene compounds, especially methoxymethylene compounds, from substituted or unsubstituted acetic acid alkyl esters, especially acetic acid methyl esters, comprising reacting a corresponding hydroxymethylene compound of the substituted or unsubstituted acetic acid alkyl ester or its alkali salt with excess alkanol, preferably methanol, in the presence of HCl and a water-binding agent out of the group of
   (a) 1 to 2 moles, per mole of starting material, of an alkyl nitrile, preferably acetonitrile, methanol and HCl, and/or
   (b) 0.5 to 2 moles, per mole of water formed, of silicic acid tetraalkyl esters, e.g., tetramethoxysilane, and/or
   (c) 0.5 to 2 moles, per mole of water formed, of a mixture of silicon tetrachloride and an alkanol, preferably methanol; at a temperature from 20° to 50° C.

2. The method of claim 1, wherein the reaction is perfromed in a mixture of alkanol, preferably methanol, and silicon tetrachloride.

3. The method of claim 1, wherein a mixture of enol ether and acetal obtained in the reaction is transformed thermally and/or in the presence of acid catalysts to pure enol ether.

4. The method of claim 1, wherein 0.5 to 2.0 moles of silicon tetrachloride or $Si(OCH_3)_4$, preferably 0.6 to 1.1 moles are used per mole of formed water.

5. The method of claim 1, wherein 1.0 to 2.0 moles, preferably 1.05 to 1.25 moles of nitrile are used per mole of formed water.

6. The method of claim 3, wherein the acetals formed in the reaction are transformed at 100° to 200° C., preferably 140° to 155° C., to the enol ethers.

7. The method of claim 6, wherein the acid catalysts for the splitting off of methanol are used in an amount of 0.1 to 10 wt. %, preferably of 0.9 to 2.5 wt. %, with respect to the amount of the acetals.

8. The method of claim 1, wherein a reaction solution from the preparation of the alkali salts of the hydroxymethylene compounds by formylation serves as the corresponding hydroxymethylene compound for reaction with the excess alkanol.

9. The method of claim 1, wherein the HCl is formed in situ.

* * * * *

UNITED STATES PATENT AND TRADEMARK OFFICE
CERTIFICATE OF CORRECTION

PATENT NO.  : 4,665,218

DATED       : May 12, 1987

INVENTOR(S) : Fritz Englaender et al

It is certified that error appears in the above-identified patent and that said Letters Patent is hereby corrected as shown below:

Column 4, line 30 "948" should read -- 1948 --

Column 5, line 7 after "a" insert --carbon dioxide pressure of 50 bar, a mixture of 166.4 g of methoxyacetic acid methyl ester and 355 g of methyl formate--.

Signed and Sealed this

Tenth Day of April, 1990

Attest:

HARRY F. MANBECK, JR.

*Attesting Officer*    *Commissioner of Patents and Trademarks*